(12) United States Patent
Do

(10) Patent No.: US 9,889,203 B2
(45) Date of Patent: *Feb. 13, 2018

(54) CHEMICAL CROSSLINKERS

(71) Applicant: AMICUS THERAPEUTICS, INC., Cranbury, NJ (US)

(72) Inventor: Hung Do, New Hope, PA (US)

(73) Assignee: AMICUS THERAPEUTICS, INC., Cranbury, NJ (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/762,647

(22) PCT Filed: Mar. 14, 2014

(86) PCT No.: PCT/US2014/027818
§ 371 (c)(1),
(2) Date: Jul. 22, 2015

(87) PCT Pub. No.: WO2014/143734
PCT Pub. Date: Sep. 18, 2014

(65) Prior Publication Data
US 2016/0129126 A1    May 12, 2016

Related U.S. Application Data

(60) Provisional application No. 61/794,784, filed on Mar. 15, 2013.

(51) Int. Cl.
| | | |
|---|---|---|
| *A61K 47/48* | (2006.01) | |
| *C07K 14/65* | (2006.01) | |
| *C12N 9/16* | (2006.01) | |
| *C12N 9/20* | (2006.01) | |
| *C12N 9/24* | (2006.01) | |
| *C12N 9/26* | (2006.01) | |
| *C12N 9/42* | (2006.01) | |
| *C12N 9/40* | (2006.01) | |
| *A61K 38/30* | (2006.01) | |
| *A61K 38/47* | (2006.01) | |
| *C12N 9/96* | (2006.01) | |

(52) U.S. Cl.
CPC ........ *A61K 47/48215* (2013.01); *A61K 38/30* (2013.01); *A61K 38/47* (2013.01); *C07K 14/65* (2013.01); *C12N 9/16* (2013.01); *C12N 9/20* (2013.01); *C12N 9/2402* (2013.01); *C12N 9/2408* (2013.01); *C12N 9/2434* (2013.01); *C12N 9/2465* (2013.01); *C12N 9/2488* (2013.01); *C12N 9/96* (2013.01); *C07K 2319/00* (2013.01); *C12Y 302/0102* (2013.01)

(58) Field of Classification Search
None
See application file for complete search history.

(56) References Cited

U.S. PATENT DOCUMENTS

| | | | |
|---|---|---|---|
| 9,545,450 B2 * | 1/2017 | Do ......................... | C07K 14/65 |
| 2015/0037311 A1 * | 2/2015 | Boivin ............. | A61K 47/48246 |
| | | | 424/94.6 |

FOREIGN PATENT DOCUMENTS

| | | |
|---|---|---|
| WO | WO 01/70685 A2 | 9/2001 |
| WO | WO 01/70685 A3 | 9/2001 |
| WO | WO 2006/108052 A2 | 10/2006 |
| WO | WO 2006/108052 A3 | 10/2006 |
| WO | 2012/166653 A2 | 12/2012 |

OTHER PUBLICATIONS

Partial Supplementary European Search Report dated Jul. 13, 2016 in Patent Application No. 14764160.9.
"Next Generation Conjugation Reagents & Services", Aug. 2007 Catalog & Reference Manual, XP-002759217, 2007, 116 Pages.
Solulink, "A New Generation of Peptide Conjugation Products," //www.solulink.com/white_papers/peptide.pdf, Jul. 13, 2012 [according to document properties for posted document], 14 pages.
International Search Report and Written Opinion dated Oct. 10, 2014 in PCT/US2014/027818 filed Mar. 14, 2014.

* cited by examiner

*Primary Examiner* — Anand U Desai
(74) *Attorney, Agent, or Firm* — Oblon, McClelland, Maier & Neustadt, L.L.P.

(57) ABSTRACT

Disclosed herein are methods of chemical conjugation comprising contacting a lysosomal enzyme with a first crosslinking agent to introduce aldehyde groups; contacting a lysosomal targeting peptide with a second crosslinking agent to introduce a hydrazide group at the N-terminal residue; contacting the lysosomal enzyme with aldehyde groups of step a. with the lysosomal targeting peptide with a hydrazide group at the N-terminal residue of step b; and forming a lysosomal enzyme-lysosomal targeting peptide conjugate.

8 Claims, 9 Drawing Sheets

Acetone-protected NHS-PEG$_4$-hydrazide

Dimethylbenzyloxycarbonyl-protected NHS-PEG$_4$-hydrazide

Trimethylbenzyloxycarbonyl-protected NHS-PEG$_4$-hydrazide

CHEMICAL CROSSLINKERS

This application claims the benefit of U.S. Ser. No. 61/794,784 filed Mar. 15, 2013

FIELD OF THE INVENTION

The disclosed inventions relate generally to compositions and methods for chemical crosslinking.

BACKGROUND

Lysosomes are specialized intracellular organelles where proteins, various lipids (including glycolipids and cholesterol) and carbohydrates are degraded and recycled to their primary constituents that enable synthesis of new proteins, membrane components and other molecules. Lysosomes are also utilized by cells to help maintain homeostasis and cellular health through an adaptive cellular process known as autophagy that increases lysosomal activity to provide additional amino acids for increased biosynthesis of various proteins (e.g., antibodies and interferons) and to supply nutrients for energy production to deal with stressful periods of nutrient deprivation or viral infections. Each metabolic process is catalyzed by a specific resident lysosomal enzyme. Genetic mutations can cause deficiencies in lysosomal biological activities that alter metabolic processes and lead to clinical diseases. Lysosomal storage disorders (LSDs) are a class of approximately 50 different human metabolic diseases caused by a deficiency for specific lysosomal proteins that results in the accumulation of various substances within the endosomal/lysosomal compartments. Many of these diseases have been well-characterized to understand the deficient lysosomal protein and the resultant metabolic defect. For example, there are several LSDs of altered glycolipid catabolism such as Gaucher, Fabry, and Tay-Sachs/Sandhoff. Neimann-Pick C is characterized by impaired lipid and cholesterol metabolism while diseases of altered carbohydrate metabolism such as glycogen storage diseases type II (Pompe) and type III (Corey-Forbes) have also been characterized. Other LSDs alter metabolism of bone or extracellular matrices [e.g., mucopolysaccharidoses (MPS I-VII), Gaucher] and protein turnover (neuronal ceroid lipofuscinoses; Batten, etc.). While LSDs are relatively rare, they can cause severe chronic illness and often death if not effectively treated.

There are no known cures for lysosomal storage diseases but a number of different treatment approaches have been investigated for various LSDs including bone marrow and umbilical cord blood transplantation, enzyme replacement therapy (ERT), substrate reduction therapy (SRT) and pharmacological chaperone therapy. Gene therapy is also being developed but has not been tested clinically. Of these treatment approaches, ERT is the most established with multiple ERTs approved for the treatment of various LSDs including Gaucher, Fabry, Pompe, MPS I, MPS II and MPS VI while one SRT drug is approved for the treatment of Gaucher disease.

The concept of ERT for the treatment of a lysosomal storage disease is fairly straightforward where a recombinant human lysosomal enzyme is administered in patients to supplement the deficient biological activity and improve clinical symptoms. However, unlike other protein therapeutic treatments that function primarily at the cell surface or outside of cells (e.g., anti-VEGF and other antibodies, erythropoietin, clotting factors, etc.), lysosomal enzymes must function inside cells, within lysosomes, and therefore use a mechanism for entering cells from the outside and subsequent delivery to these internal compartments. In mammals, the branched carbohydrate structures on the protein backbone on certain asparagine residues (N-linked oligosaccharides; N-glycans) for most soluble lysosomal enzymes are post-translationally modified to form a specialized carbohydrate structure called mannose 6-phosphate (M6P). M6P is the natural biological signal for identification and transport of newly synthesized lysosomal proteins from the Golgi apparatus to lysosomes via membrane-bound M6P receptors. A class of M6P receptors (cation-independent M6P receptor; CI-MPR) also cycles to the plasma membrane and is functionally active for binding and internalizing exogenous lysosomal proteins. The CI-MPR is believed to have evolved to recapture lysosomal proteins that escaped cells (via secretion out of cells) and thus, provide a targeting mechanism for internalizing exogenous lysosomal proteins and is the basis for enzyme replacement therapy for various LSDs.

Recombinant lysosomal enzyme replacement therapies have been shown to be generally safe but their effectiveness for reducing clinical symptoms varies widely. For example: Fabrazyme™ (recombinant acid α-galactosidase A; Genzyme Corp.) ERT dosed at 1 mg/kg body weight every other week is sufficient to clear accumulated substrate from endothelial cells in Fabry disease while 40 mg/kg of Myozyme™ (recombinant human acid α-glucosidase, rhGAA; Genzyme Corp.) dosed every other week is only moderately effective for Pompe disease. The disparate efficacy is primarily attributed to differences in the M6P content such that low levels of M6P correlates with poor drug targeting and lower efficacy. The manufacture of recombinant lysosomal enzymes is very challenging because it is extremely difficult to control carbohydrate processing, particularly the level of M6P in mammalian expression systems. Two specialized Golgi enzymes catalyze the M6P modification; N-acetylglucosamine phosphotransferase adds phosphate-linked N-acetylglucosamine onto certain terminal mannose residues while N-Acetylglucosamine-1-phosphodiester α-N-acetylglucosaminidase (also known as Uncovering Enzyme) removes the covering N-acetylglucosamine to reveal the M6P signal. However, N-acetylglucosamine phosphotransferase is limiting in cells and this biochemical reaction is inherently inefficient for various lysosomal proteins. Overexpression of lysosomal proteins during the manufacturing process greatly exacerbates this problem and leads to highly variable amounts of M6P. Consequently, carbohydrate processing is typically incomplete and leads to the production of recombinant lysosomal enzymes with mixtures of N-glycans that contain M6P, non-M6P structures of high-mannose type N-glycans and complex-type N-glycans (typical for secretory proteins). To complicate matters, dead or damaged cells release enzymes such as phosphatases into the cell culture medium which remove M6P. Consequently, reduced M6P content lowers the binding affinity of a recombinant lysosomal enzyme for M6P receptors and decreases its cellular uptake and thereby, reduce drug efficacy. Dead or damaged cells release other glycosidases that remove other carbohydrates (e.g., sialic acids, galactose, etc.) to reveal internal carbohydrates that are not typically exposed and these N-glycans are readily identified as aberrant. These incomplete N-glycan structures increase the clearance rate of recombinant lysosomal proteins from the circulation which can also reduce drug efficacy. Higher drug doses are therefore necessary to compensate for reduced efficacy. Higher drug dose requirements however have multiple negative implications: (1) higher drug dose could be costprohibitive by increasing an already expensive treatment; (2) high drug doses require long infusion times; (3) large amounts of circulating drug results in significant antibody responses (seen in most Pompe patients) and numerous patients have also experienced allergic reactions during infusions. The FDA has issued a "black-label warning" for Myozyme and the drug is typically administered very slowly at the beginning but ramped up over the course of the infusion. This strategy helps to mitigate the allergic responses but significantly lengthens infusion times where 12-hr infusions are not uncommon.

One potential strategy for improving drug targeting for various lysosomal ERTs employs a targeting peptide to efficiently target ERTs to lysosomes without requiring the traditional M6P carbohydrate structures. This is conceptually feasible since the cation-independent M6P receptor contains a distinct binding domain for a small peptide called insulin-like growth factor 2 (IGF-2) and this receptor is therefore known as the IGF-2/(IGF-2/CI-MPR). This receptor is in fact solely responsible for internalizing exogenous M6P-bearing lysosomal proteins because the IGF-2/CI-MPR is present and biologically active on the cell surface. The other class of M6P receptors, the cation-dependent M6P receptor (CD-MPR), is only involved in the transport of lysosomal proteins within cells because it is not biologically active on cell surfaces and lacks the IGF-2 peptide binding domain. The IGF-2/CI-MPR has two separate binding sites for M6P (domains 1-3 and 7-9, respectively) such that it binds a mono-M6P N-glycan (1 M6P residue on N-glycan) with moderate affinity or a bis-M6P N-glycan (two M6P residues on the same N-glycan) with approximately 3000-fold higher affinity. Since lysosomal proteins contain mixtures of complex (no M6P), mono- and bis-M6P N-glycans, their affinities for the IGF-2/CI-MPR vary widely depending on the type and amount of M6P-bearing N-glycans.

There remains a need to develop strategies to create IGF-2-linked proteins for improved protein targeting. There remains a need for constructs that maintain the correct protein conformation.

SUMMARY OF THE INVENTION

Disclosed herein are methods of chemical conjugation comprising a) contacting a lysosomal enzyme with a first crosslinking agent to introduce aldehyde groups; b) contacting a lysosomal targeting peptide with a second crosslinking agent to introduce a hydrazide group at the N-terminal residue; contacting the lysosomal enzyme with aldehyde groups of step a) with the lysosomal targeting peptide with a hydrazide group at the N-terminal residue of step b); and forming a lysosomal enzyme-lysosomal targeting peptide conjugate.

Also provided herein are bifunctional crosslinkers comprising acetone-, dimethylbenzyloxycarbonyl-, trimethylbenzyloxycarbonyl-protected hydrazide groups, or any combination thereof. Also provided herein are modified lysosomal targeting peptides comprising a protected hydrazide group.

Disclosed herein are methods of making a modified lysosomal targeting peptide, comprising: contacting a lysosomal targeting peptide with a crosslinking agent to introduce a hydrazide group at the N-terminal residue. Also provided are methods of linking one or more lysosomal targeting peptides to a lysosomal enzyme comprising deprotecting a hydrazide-modified lysosomal targeting peptide in solution to form a deprotected hydrazide-modified lysosomal targeting peptide; and linking at least one deprotected hydrazide modified lysosomal targeting peptide to a lysosomal enzyme.

Disclosed herein are lysosomal enzyme-lysosomal targeting peptide conjugates, comprising: a lysosomal enzyme crosslinked to one or more lysosomal targeting peptides via one or more bifunctional crosslinkers.

BRIEF DESCRIPTION OF THE DRAWINGS

The present disclosure is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

FIG. 4A shows the retention time for vIGF2 peptide upon attachment of tBoc-protected hydrazide linker (middle panel) relative to the starting unmodified vIGF2 peptide (upper panel) and removal of the tBoc protection group was shown to cause another shift (decrease) in the retention on C4 RP-HPLC (lower panel). FIG. 4B shows the results of vIGF2 peptide-conjugated rhGAA (via resultant hydrazone linkage) in an IGF2/CI-MPR receptor plate binding assays.

FIGS. 5A and 5B show the evaluation of cellular uptake for hydrazone linked vIGF2-rhGAA by internalization of exogenous unconjugated rhGAA (10-500 nM) and vIGF2-rhGAA (2-50 nM) in L6 rat skeletal muscle myoblasts. FIG. 5A: vIGF2-rhGAA was shown to be internalized substantially better than unconjugated rhGAA in L6 myoblasts at all protein concentrations tested. FIG. 5B: L6 myoblast lysates were analyzed by Western blotting using rabbit anti-human GAA polyclonal primary antibodies.

FIG. 6 shows retention time in a C4 RP-HPLC assay of purified vIGF2 peptide chemically modified with a 20-fold molar excess of the bifunctional crosslinker methylbenzyloxy carbonyl (BOM)-protected hydrazide (NHS-PEG4-BOM-hydrazide) to introduce BOM-protected hydrazide functional group at N-terminus of peptide.

FIG. 7A shows retention time in a C4 RP-HPLC assay of purified vIGF2 peptide chemically modified with a 20-fold molar excess of the bifunctional crosslinker Phthalimidooxy-PEG12-NHS ester to introduce a phthalimidooxy functional group at N-terminus of peptide. FIG. 7B shows affinity assays of oxime-linked vIGF2-rhGAA in an IGF2/CI-MPR receptor plate binding assays to determine whether attached vIGF2 peptide improved rhGAA affinity for the IGF2/CI-MPR receptor.

FIG. 8 shows retention time in a C4 RP-HPLC assay of purified vIGF2 peptide chemically modified with a 20-fold molar excess of the bifunctional crosslinker tBoc-aminooxy-$PEG_{12}$-PFB to introduce a tBoc-protected aminooxy functional group at N-terminus of peptide.

FIG. 9 shows IGF2/CI-MPR receptor plate binding assays of aminooxy-modified vIGF2 peptide directly conjugated to chemically oxidized rhGAA (containing chemically reactive aldehyde groups on carbohydrates) to form the resultant oxime linkages.

DETAILED DESCRIPTION OF ILLUSTRATIVE EMBODIMENTS

Figure 1:
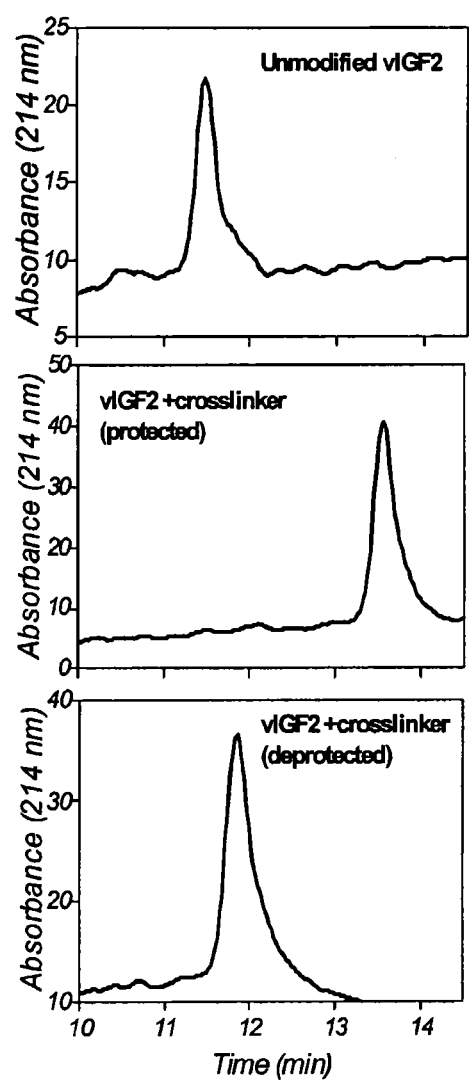
FIG. 1 shows the modification of the vIGF2 peptide as monitored on an HPLC system.

The present subject matter can be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

The chemical conjugation approach can be improved by novel bifunctional crosslinkers which can be utilized for modification of vIGF2 peptide to introduce a protected hydrazide group. The acid labile protecting groups can be efficiently removed using mild acidic buffers for better recovery of modified vIGF2 peptide. The deprotected hydrazide-modified vIGF2 peptide can then be lyophilized and stored as a dried powder to preserve the chemical reactivity of the hydrazide moiety. The deprotected hydrazide-modified vIGF2 peptide can be stored indefinitely until chemical coupling to lysosomal enzymes. These novel crosslinkers can therefore provide significantly more stable components and better control of chemical conjugation process to enable scale up of process.

This chemical conjugation approach involves modifying the amino (N)-terminus and one or more lysine residues on a recombinant human lysosomal enzyme using a first crosslinking agent to introduce novel acetone-protected hydrazide groups on recombinant human lysosomal enzymes. The first crosslinking agent modified recombinant human lysosomal enzyme can then be purified to remove excess crosslinkers and reaction byproducts. The purification can be performed using acidic pH buffers which preserves catalytic activity for lysosomal enzyme and displaces the acetone protecting group to expose the chemically reactive hydrazide groups. Separately, the amino (N)-terminus of a short extension linker region preceding vIGF2 peptide can be modified using a second crosslinking agent to introduce novel chemically reactive aldehyde group on vIGF2 peptide. The modified vIGF2 peptide can then be purified to remove excess crosslinkers and reaction byproducts and then lyophilized. In a final coupling reaction, the hydrazide-modified recombinant human lysosomal enzyme can be added directly to the lyophilized aldehyde-modified vIGF2 peptide to generate the vIGF2-enzyme conjugate. While this method is effective to generate vIGF2-enzyme conjugates, the final chemical conjugation reaction is preferably performed rapidly because the introduced hydrazide groups are not stable in aqueous solutions and thus, the chemical reactivity is diminished over a relatively short time (within 1-2 days). The scale up of process can therefore be challenging if the modification of lysosomal enzymes with bifunctional crosslinker and purification of hydrazide-modified lysosomal enzymes cannot be quickly completed (preferably within 1 day).

It would be preferable to change the order of modification whereby the lysosomal enzyme can be modified with a crosslinking agent to introduce aldehyde groups and the vIGF2 peptide would be modified with a crosslinking agent to introduce hydrazide. However, a majority of hydrazide-containing crosslinkers such as succinimidyl 6-hydrazinonicotinate acetone (S-Hynic) or related crosslinkers cause aggregation and/or precipitation of vIGF2 peptide and lead to significant loss of peptide. Appropriate crosslinkers and methods to modify vIGF2 peptide with bifunctional crosslinkers to introduce a protected hydrazide group on vIGF2 peptide are provided herein. The protecting group can be subsequently removed by incubation in acidic buffers and the hydrazide-modified vIGF2 peptide can be purified by reverse phase chromatography on HPLC. The purified hydrazide-modified vIGF2 peptide can then be lyophilized and stored as a dried powder. This strategy ensures that the hydrazide group remains chemically active for coupling to lysosomal enzymes. In a separate reaction, a recombinant lysosomal enzyme can be modified with a crosslinking agent to introduce novel aldehyde groups. After purification to remove excess crosslinker and reaction byproducts, the aldehyde-modified lysosomal enzymes can then be stored until coupling to vIGF2 peptide because the introduced aldehyde groups are chemically stable in aqueous solutions. This new strategy provides "hold steps" in the process where individual components (modified lysosomal enzyme and modified vIGF2) can be stored indefinitely until coupling to generate the vIGF2-enzyme conjugates. This new method therefore generates the individual components with substantially higher stability and provides better overall control of conjugation process which is conducive to scale up of process.

Suitable methods of chemical conjugation can comprise a) contacting a lysosomal enzyme with a first crosslinking agent to introduce aldehyde groups; b) contacting a lysosomal targeting peptide with a second crosslinking agent to introduce a hydrazide group at the N-terminal residue; contacting the lysosomal enzyme with aldehyde groups of step a) with the lysosomal targeting peptide with a hydrazide group at the N-terminal residue of step b); and forming a lysosomal enzyme-lysosomal targeting peptide conjugate.

The lysosomal targeting peptide may suitably comprise variant insulin-like growth factor 2 (vIGF2), preferably a variant of human insulin-like growth factor 2. In one embodiment, such a variant IGF 2 may include amino acid deletions and substitutions that permit vIGF2 peptide to maintain high affinity for the IGF-2/CI-MPR while reducing peptide binding affinity to IGF-1 and Insulin receptors. For example, the deletions and substitutions may comprises one or more of the following changes: deletion of N-terminal amino acid residues 1-4 since these residues are not needed for binding intended IGF2/CI-MPR receptor and also eliminates a proline at position 4 and the associated bend or kink in the protein at the N-terminus; glutamic acid residue at position 6 of wildtype human IGF2 substituted with arginine for reducing or eliminating peptide binding to serum IGF binding proteins (IGFBPs), tyrosine residue of wildtype human IGF 2 at position 27 substituted with leucine for reducing or eliminating peptide binding the insulin and IGF-1 receptors, and the lysine residue at position 65 of human IGF-2 substituted with arginine to prevent chemical modification of peptide at that position.

In still further embodiments, the variant IGF2 can include or be one of the following sequences:

```
                                                SEQ ID NO: 1
AYRPSETLCGGELVDTLQFVCGDRGFYFSRPASRVSRRSRGIVEECCFR
SCDLALLETYCATPAKSE

SEQ ID NO: 2
SRTLCGGELVDTLQFVCGDRGFLFSRPASRVSRRSRGIVEECCFRSCDL
ALLETYCATPARSE

SEQ ID NO: 3
GGGGSRTLCGGELVDTLQFVCGDRGFLFSRPASRVSRRSRGIVEECCFR
SCDLALLETYCATPARSE

SEQ ID NO: 4
GGGGSGGGGSRTLCGGELVDTLQFVCGDRGFLFSRPASRVSRRSRGIVE
ECCFRSCDLALLETYCATPARSE
```

Suitable first crosslinking agents include N-succinimidyl-4-formylbenzamide (S-4FB). A suitable second crosslinking agent includes N-tert-butoxycarbonyl (tBoc)-protected hydrazide crosslinker (NHS-PEG4-tBoc-hydrazide) or a methoxybenzyloxy carbonyl (BOM)-protected hydrazide (NHS-PEG4-BOM-hydrazide). In other suitable embodiments the second crosslinking agent can include acetone-, dimethylbenzyloxycarbonyl-, trimethylbenzyloxycarbonyl-protected hydrazide groups, or any combination thereof. In other suitable embodiments the bifunctional crosslinker can include acetone-protected NHS-PEG4-hydrazide, dimethylbenzylcarbonyl-protected NHS-PEG4-hydrazide, trimethylbenzyloxycarbonyl-protected NHS-PEG4-hydrazide, or any combination thereof.

Suitable lysosomal enzymes include acid α-glucosidase (rhGAA), acid α-galactosidase A (GLA), acid β-glucuronidase (GUS), acid α-iduronidase A (IduA), acid iduronidate 2-sulfatase (I2S), β-hexosaminidase A (HexA), β-hexosaminidase B (HexB), acid α-mannosidase A, β-glucocerebrosidase (GlcCerase), acid lipase (LPA), or any combination thereof. In other suitable embodiments the lysosomal enzyme can be mammalian and the mammalian lysosomal enzyme can be human.

The lysosomal targeting peptide with a hydrazide group at the N-terminal residue is typically added to the lysosomal enzyme at about four-fold molar excess. Aniline can also be suitably added at that time. The methods provided herein can further comprise one or more purification steps of the lysosomal enzyme-lysosomal targeting peptide conjugate. For example, purification can be carried out using size-exclusion chromatography.

The methods provided herein can further comprise evaluating the lysosomal enzyme-lysosomal targeting peptide conjugate's ability to bind the IGF2/CI-MPR receptor. Binding of the lysosomal enzyme-lysosomal targeting peptide conjugate typically saturates at or above about 25 nM of lysosomal enzyme-lysosomal targeting peptide conjugate. Accordingly, the lysosomal enzyme-lysosomal targeting peptide conjugate can maintain the correct protein confirmation by enabling high affinity binding to the IGF2/CI-MPR receptor.

Suitable bifunctional crosslinkers can comprise acetone-, dimethylbenzyloxycarbonyl-, trimethylbenzyloxycarbonyl-protected hydrazide groups, or any combination thereof. In other suitable embodiments the bifunctional crosslinker can comprise Acetone-protected NHS-PEG4-hydrazide, Dimethylbenzylcarbonyl-protected NHS-PEG4-hydrazide, Trimethylbenzyloxycarbonyl-protected NHS-PEG4-hydrazide, or any combination thereof.

Suitable modified lysosomal targeting peptides can comprise a protected hydrazide group. In other suitable embodiments the modified lysosomal targeting peptide can comprise modified vIGF2 peptide. In other suitable embodiments the hydrazide group is protected by acetone-, dimethylbenzyloxycarbonyl-, trimethylbenzyloxycarbonyl-groups, or any combination thereof. In other suitable embodiments the modified lysosomal targeting peptide is in a powder. In other suitable embodiments the modified lysosomal targeting peptide is lyophilized.

Suitable methods of making a modified lysosomal targeting peptide include contacting a lysosomal targeting peptide with a crosslinking agent to introduce a hydrazide group at the N-terminal residue. A suitable lysosomal targeting peptide is vIGF2. A suitable crosslinking agent includes N-tert-butoxycarbonyl (tBoc)-protected hydrazide crosslinker (NHS-PEG4-tBoc-hydrazide). The crosslinking agent can comprise acetone-, dimethylbenzyloxycarbonyl-, trimethylbenzyloxycarbonyl-protected hydrazide groups, or any combination thereof. The bifunctional crosslinker can comprises acetone-protected NHS-PEG4-hydrazide, dimethylbenzylcarbonyl-protected NHS-PEG4-hydrazide, trimethylbenzyloxycarbonyl-protected NHS-PEG4-hydrazide, or any combination thereof. The methods provided herein can further comprise deprotecting the protected hydrazide groups of the modified lysosomal targeting peptide. As well, a further step of lyophilizing the modified lysosomal targeting peptide can be implemented to form a powder.

Suitable methods of linking one or more lysosomal targeting peptides to a lysosomal enzyme can comprise deprotecting a hydrazide-modified lysosomal targeting peptide in solution to form a deprotected hydrazide-modified lysosomal targeting peptide; and linking at least one deprotected hydrazine modified lysosomal targeting peptide to a lysosomal enzyme. The lysosomal targeting peptide can comprise vIGF2, and the lysosomal enzyme can comprise acid α-glucosidase (rhGAA), acid α-galactosidase A (GLA), acid β-glucuronidase (GUS), acid α-iduronidase A (IduA), acid iduronidate 2-sulfatase (I2S), β-hexosaminidase A (HexA), β-hexosaminidase B (HexB), acid α-mannosidase A, β-glucocerebrosidase (GlcCerase), acid lipase (LPA), or any combination thereof.

Suitable lysosomal enzyme-lysosomal targeting peptide conjugates can comprise a lysosomal enzyme crosslinked to one or more lysosomal targeting peptides (e.g., vIGF2) via one or more bifunctional crosslinkers. Suitable bifunctional crosslinkers can comprise acetone-protected NHS-PEG4-hydrazide, dimethylbenzylcarbonyl-protected NHS-PEG4-hydrazide, trimethylbenzyloxycarbonyl-protected NHS-PEG4-hydrazide, N-succinimidyl-4-formylbenzamide (S-4FB), or any combination thereof. The lysosomal enzyme suitably comprises acid α-glucosidase (rhGAA), acid α-galactosidase A (GLA), acid β-glucuronidase (GUS), acid α-iduronidase A (IduA), acid iduronidate 2-sulfatase (I2S), β-hexosaminidase A (HexA), β-hexosaminidase B (HexB), acid α-mannosidase A, β-glucocerebrosidase (GlcCerase), acid lipase (LPA), or any combination thereof.

EXAMPLES

The following examples, while illustrative individual embodiments, are not intended to limit the scope of the described invention, and the reader should not interpret them in this way.

Example 1

A new chemical conjugation approach was utilized for chemical coupling of vIGF2 peptide onto lysosomal enzymes to increase their binding to the IGF2/CI-MPR receptor. This approach is different from what had been previously described such that the lysosomal enzymes are modified with a first crosslinking agent to introduce aldehyde groups while vIGF2 peptide is modified with a second crosslinking agent to introduce a hydrazide group at the N-terminal residue. Specifically, recombinant wildtype human acid α-glucosidase (rhGAA) was concentrated to 7.5 mg/ml via a concentrator device equipped with a 50 kDa molecular weight cutoff membrane and then buffer exchanged into 50 mM sodium phosphate (pH 6.5)/100 mM NaCl/0.05% polysorbate-80 by dialysis at 4° C. overnight. rhGAA was then chemically modified with a 20-fold molar excess of N-succinimidyl-4-formylbenzamide (S-4FB; Solulink) crosslinker for 2 hrs at ambient temperature to introduce novel benzaldehyde groups. The benzaldehyde-modified rhGAA is then purified in 50 mM NaOAc (pH 4.8)/50 mM NaCl buffer to remove excess crosslinker and reaction byproducts and stored at 4° C. until chemical coupling to vIGF2 peptide.

In a separate reaction, purified vIGF2 peptide was reconstituted at 0.6 mg/ml in 50 mM sodium phosphate (pH 7.5)/50 mM NaCl/0.05% polysorbate-80 and modified with a 20- to 40-fold molar excess of N-tert-butoxycarbonyl (tBoc)-protected hydrazide crosslinker (NHS-PEG4-tBoc-hydrazide; Quanta Biodesign). The modification of vIGF2 peptide was monitored using a using a 4.6×250 mm, 5 μm, 300 Å C4 Jupiter column (Phenomenex, Torrence, Calif.) on an Agilent Technologies (Palo Alto, Calif.) HPLC system (C4 RP-HPLC) as shown in FIG. 1. Mobile phases consisted of Buffer A (0.1% TFA in water) and Buffer B [0.1% TFA in acetonitrile (MeCN)]. This analytical method, designated as C4 reverse phase HPLC (C4 RP-HPLC), was utilized to characterize IGF2 peptide samples by injecting 5-100 μL samples on the C4 column pre-equilibrated with 74% Buffer A, 26% Buffer B at 2 mL/min Two minutes after sample injection, a linear gradient of 26% to 33% Buffer B was developed over 13 minutes. Under these conditions, unmodified vIGF2 peptide elutes at approximately 11.5 minutes. As the crosslinker is chemically attached to vIGF2 during the modification reaction, the modified IGF2 peptide has a distinct chromatographic profile and appears as a new later eluting peak on C4 RP-HPLC with an apparent retention time of ~13.5 min. When vIGF2 peptide was >95% modified with crosslinker, the reaction was halted by adding TFA (15% final concentration) and incubated for up to 4 hrs. This incubation step was used to remove the tBoc protecting group as evidenced by the significant shift in the retention time of vIGF2 on C4 RP-HPLC. Under these experimental conditions, approximately 50% of the tBoc was removed. Significant loss of the modified vIGF2 peptide occurred when using longer incubations or higher TFA concentrations. The hydrazide-modified vIGF2 peptide was then purified via a preparative C4 RP-HPLC, lyophilized and stored as a dried powder and stored at 4° C. until chemical coupling to rhGAA.

The benzaldehyde-modified rhGAA was chemically conjugated to the deprotected hydrazide-modified vIGF2 peptide in a final reaction by adding the lysosomal enzyme directly to the lyophilized peptide at a 4-fold molar excess of peptide. Aniline, a chemical catalyst of this reaction, was added to a final concentration of 10 mM and the reaction was incubated overnight at ambient temperature with gentle rocking. The vIGF2-rhGAA conjugate was purified the following day using size exclusion chromatography to remove excess vIGF2 peptide using 50 mM sodium phosphate (pH 6.2)/100 mM NaCl/0.05% (v/v) polysorbate-80 buffer.

Figure 2:
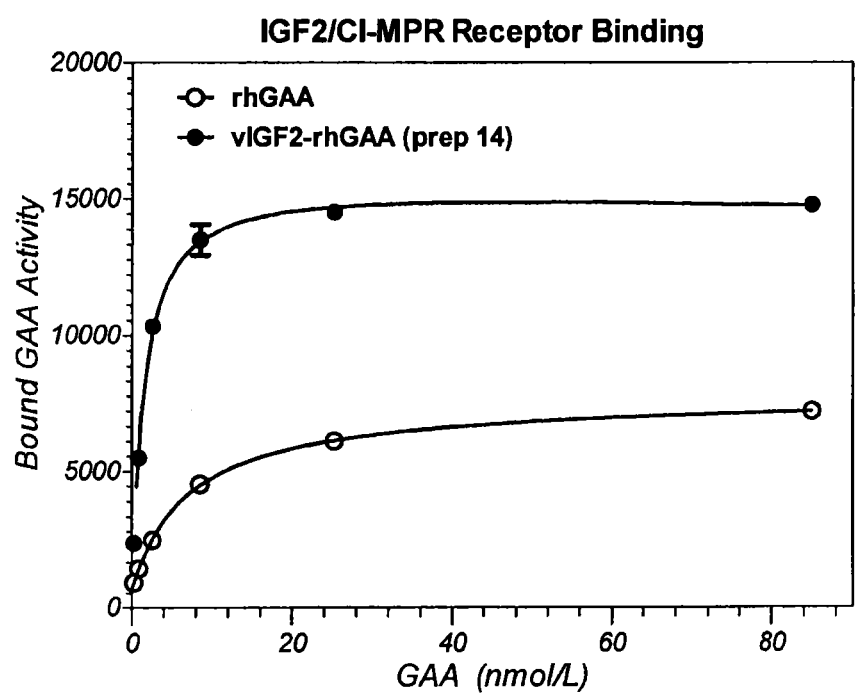
FIG. 2 shows the vIGF2-GAA conjugate's ability to bind to the IGF2-CI-MPR receptor in binding plate assays.

To determine whether the modified vIGF2 peptide retained the correct protein structure after removal of the tBoc protecting group, the vIGF2-GAA conjugate was evaluated for its ability to bind the IGF2/CI-MPR receptor in plate binding assays as shown in FIG. 2. Briefly, unconjugated rhGAA and vIGF2-rhGAA was serially diluted with Binding Buffer [40 mM HEPES (pH 6.7), 150 mM NaCl, 10 mM EDTA and 0.02% (v/v) Tween-20] to obtain final GAA concentrations ranging from 0.01-10 μg/ml and incubated in IGF2/CI-MPR receptor coated plates at 37° C. for 30 min. The receptor plate was washed 3× with Binding Buffer to remove unbound enzyme and the amount of bound GAA enzyme was measured using the fluorogenic 4-methylumbeliferyl-α-glucose substrate[4-MU-α-Glc; 1 mM final substrate concentration in 50 μl 0.1M NaOAc (pH 4.8)]. Forty five μL of the reaction samples were then transferred to new 96-well black, clear bottom assay plates and 125 μL 0.5 M NaOH was added to stop the enzymatic reaction and to raise the pH. The liberated 4-MU fluorescence from the individual enzymatic reactions was then quantified in a fluorescence plate reader (using 370 nm excitation and 460 emission wavelengths, respectively). As shown in FIG. 2, vIGF2-GAA bound the IGF2/CI-MPR receptor substantially better than the rhGAA starting material at all concentrations tested. The binding of vIGF2-GAA appeared to be saturated at or above 25 nM as expected. These results therefore show that vIGF2 peptide was able to maintain the correct protein conformation after removal of the tBoc deprotection group which enabled high affinity binding to the IGF2/CI-MPR receptor.

Example 2

The NHS-PEG4-tBoc-hydrazide crosslinker was shown to efficiently modify vIGF2 peptide to introduce novel hydrazide group while maintaining good solubility for the peptide. However, the tBoc protecting group was difficult to remove using mild acid conditions and used high concentrations of TFA (15%) and 4-hr incubations for deprotection. Under these harsh conditions, we were still only able to recover ~50% of the deprotected hydrazide-modified vIGF2 peptide. The approach would be further improved if crosslinkers can be designed with more labile protecting groups for efficient removal and better recovery of modified peptide.

Figure 3:
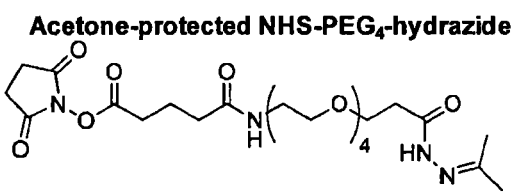
FIG. 3 shows the chemical structures of some of the disclosed crosslinkers.
Figure 3:
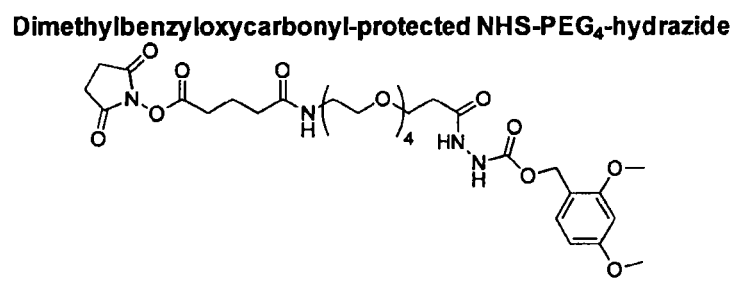
Figure 3:
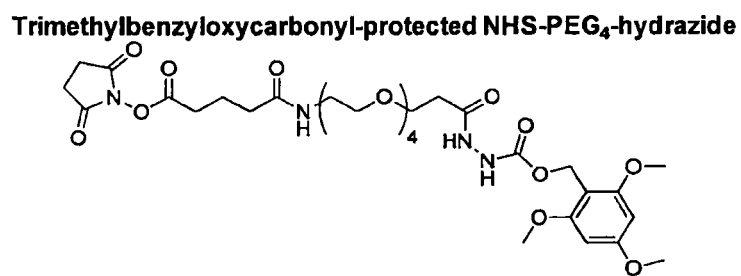

Novel bifunctional crosslinkers have been developed for efficient attachment to vIGF2 peptide and to introduce protected hydrazide groups while maintaining good solubility for peptide. These new crosslinkers contain acetone-, dimethylbenzyloxycarbonyl-, or trimethylbenzyloxycarbonyl-protected hydrazide groups as shown in FIG. 3. These protecting groups are much more labile than tBoc and would use mild acid conditions (e.g., <5% TFA) for efficient removal and high recovery of the modified peptide. Moreover, these new crosslinkers should permit long-term storage of the deprotected modified vIGF2 peptide after purification and lyophilization. These new crosslinkers therefore will enable scale up and better control of the chemical conjugation process.

Example 3

Recombinant human acid α-glucosidase (rhGAA) was concentrated to 8-10 mg/ml at small scale (i.e., <100 mg) using centrifugal concentrator devices (e.g., Amicon Ultra with 50 kDa nominal molecular weight cutoff (MWCO) membrane; Millipore) and then buffer exchanged into Modification Buffer [50 mM sodium phosphate (pH 6.5)/100 mM NaCl/100 mM glucose/2% mannitol/0.05% polysorbate-80] via dialysis overnight at 4° C. For larger scale preparations (e.g., >200 mg rhGAA), protein concentration and buffer exchange can be achieved by diafiltration/concentration using a tangential flow filtration (TFF) system with a 50 kDa MWCO membrane. rhGAA protein concentration is determined by UV absorbance spectroscopy at 280 nm using the molar extinction coefficient (ε) of 166,117 $M^{-1}$ $cm^{-1}$. The rhGAA protein concentration was then adjusted to 7.5 mg/ml by dilution with Modification Buffer and incubated with a 25-fold molar excess of the bifunctional crosslinker succinimidyl 4-formylbenzoate (SFB) at about 20° C. for 4 hours to introduce novel benzaldehyde (aromatic aldehyde) groups on rhGAA. Benzaldehyde-modified rhGAA was dialyzed against 50 mM NaOAc (pH 4.8)/100 mM NaCl/0.05% polysorbate-80 at 4° C. with multiple changes of buffer to remove excess crosslinker and reaction byproducts. The chemically modified rhGAA is stable in this buffer and can be stored indefinitely until chemical conjugation to vIGF2 peptide. Importantly, the introduced benzaldehyde groups on rhGAA remain chemically reactive for conjugation to hydrazide- or aminooxy-modified vIGF2 peptide. We have also determined that benzaldehyde-modified rhGAA can be stored in 50 mM sodium phosphate (pH 6.0)/100 mM NaCl/0.05% polysorbate-80 with no adverse effects on GAA stability or coupling efficiency.

To determine the extent of chemical modification and to identify the specific amino acid residues that are modified, peptide maps from the benzaldehyde-modified rhGAA were generated and directly compared to the starting unmodified starting rhGAA sample by liquid chromatography/mass spectroscopy analysis (LC-MS). Briefly, a reference peptide map for the starting unmodified rhGAA sample was generated by digesting rhGAA into peptide fragments using a mixture of specific proteases followed by C18 reverse phase high performance liquid chromatography and analysis of individual peptide fragments by mass spectroscopy. Four different preparations of benzaldehyde-modified rhGAA were digested and processed in the same manner and compared to the reference peptide map for unmodified starting rhGAA. Our LC-MS results indicate that an average of approximately 2 novel benzaldehyde groups is introduced on rhGAA using this chemical modification procedure. Moreover, the LC-MS results show that chemical modification of rhGAA is not randomly distributed across the different lysine residues in rhGAA. Rather, chemical modification of rhGAA appears to be much more ordered and confined to a few lysine residues as shown in Table 1. The LC-MS data show that ~90% of $Lys^{902}$ is modified with the benzaldehyde moiety while approximately 50% of $Lys^{732}$ and $Lys^{838}$ are modified. A significantly smaller fraction of $Lys^{113}$ (8%) and $Lys^{161}$ (17%) are modified under these experimental conditions. The experimental error for this LC-MS analysis was estimated to be ±10%.

TABLE 1

Identification of chemically modified amino acid residues in rhGAA

| GAA Batch | Residues Modified $Lys^{113}$ | $Lys^{161}$ | $Lys^{732}$ | $Lys^{848}$ | $Lys^{902}$ | Estimated Modified Residues |
|---|---|---|---|---|---|---|
| A (Feb. 1, 2013) | 8% | 17% | 53% | 40% | 90% | 2.11 |
| B (Apr. 4, 2013) | 9% | 16% | 52% | 45% | 89% | 2.14 |
| C (Apr. 9, 2013) | 8% | 17% | 53% | 40% | 90% | 2.11 |
| D (Apr. 12, 2013) | 6% | 17% | 53% | 43% | 89% | 2.13 |
| AVE | 8 ± 1.3% | 17 ± 0.6% | 53% ± 0.6% | 42% ± 2.4% | 89% ± 0.5% | 2.12 |

The LC-MS data were informative and have very important implications for the described chemical conjugation approach. There are 15 different lysine residues within rhGAA; each theoretically has the same potential for chemical modification. Our empirical data however are contrary to this hypothesis and show that the chemical modification process appears to be much more ordered than anticipated wherein only a few, select lysine residues were consistently modified with benzaldehyde groups for 4 different batches of SFB-modified rhGAA using the method described herein. Moreover, the LC-MS data indicate that there is preferential modification of lysine residues such that $Lys^{902}$ is always modified with crosslinker while approximately half of $Lys^{732}$ and $Lys^{838}$ residues are modified with crosslinker. Only a small fraction of $Lys^{113}$ and $Lys^{161}$ were modified with benzaldehyde group. These data suggest that the observed preferential modification was dependent on the accessibility and chemical competency of individual lysine residues for chemical modification with crosslinker. For example, lysine residues may be protonated and involved with forming salt bridges (i.e., electrostatic interactions) with negatively charged aspartic acid or glutamic acid residues and not available for chemical modification. The LC-MS data suggest that $Lys^{902}$ is the most accessible and chemically competent for modification and likely the likely the first residue modified. Further, $Lys^{732}$ and $Lys^{838}$ are less accessible than $Lys^{902}$ for chemical modification but $Lys^{732}$ and $Lys^{838}$ have similar accessibility relative to each other since an approximately equivalent fraction of each is modified. These data suggest that either $Lys^{732}$ or $Lys^{838}$ is the second lysine residue modified. $Lys^{113}$ and $Lys^{161}$ are only partially accessible for chemical modification such that only a small fraction of rhGAA contains benzaldehyde at these lysine residues. No chemical modification of the amino (N—) terminus was observed for rhGAA but this enzyme is known to be naturally modified (cyclized) in cells to form pyroglutamate that is not chemically competent for modification with bifunctional crosslinkers.

These collective data indicate that the described chemical modification procedure can be utilized to reproducibly yield rhGAA with an average of 2.12 introduced benzaldehyde groups for coupling to vIGF2 peptide. Since the number of vIGF2 peptide conjugated to rhGAA is dependent on the number of introduced benzaldehyde groups, these results indicate that an average of 2 vIGF2 peptides can be conjugated to rhGAA.

After chemical modification with SFB, benzaldehyde-modified rhGAA is very stable in slightly acidic buffers such as 50 mM sodium phosphate (pH 6.0)/100 mM NaCl/0.05% polysorbate-80 or 50 mM NaOAc (pH 4.8)/100 mM NaCl/0.05% polysorbate-80 and can be stored long-term prior to chemical conjugation which is highly desirable to enable scale up of this conjugation process.

Example 4

Figure 4A:
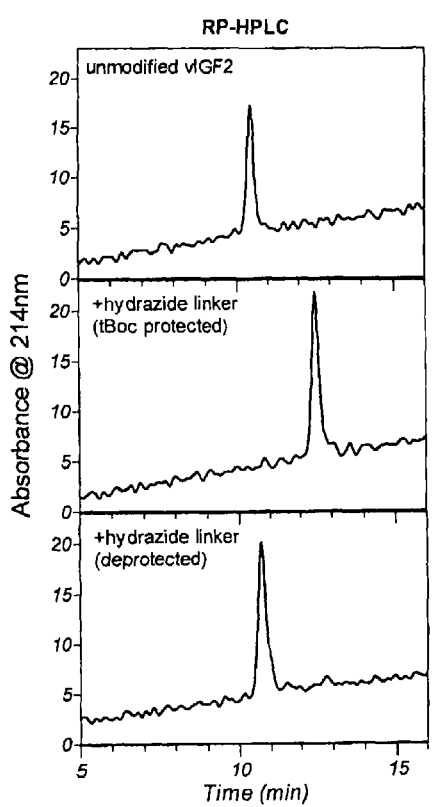
Figure 4B:
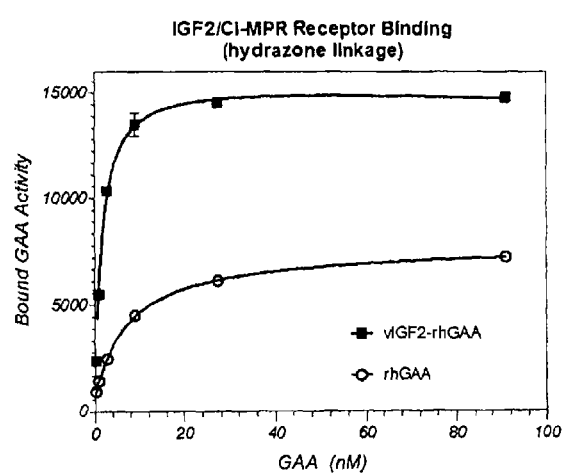
Figure 5A:
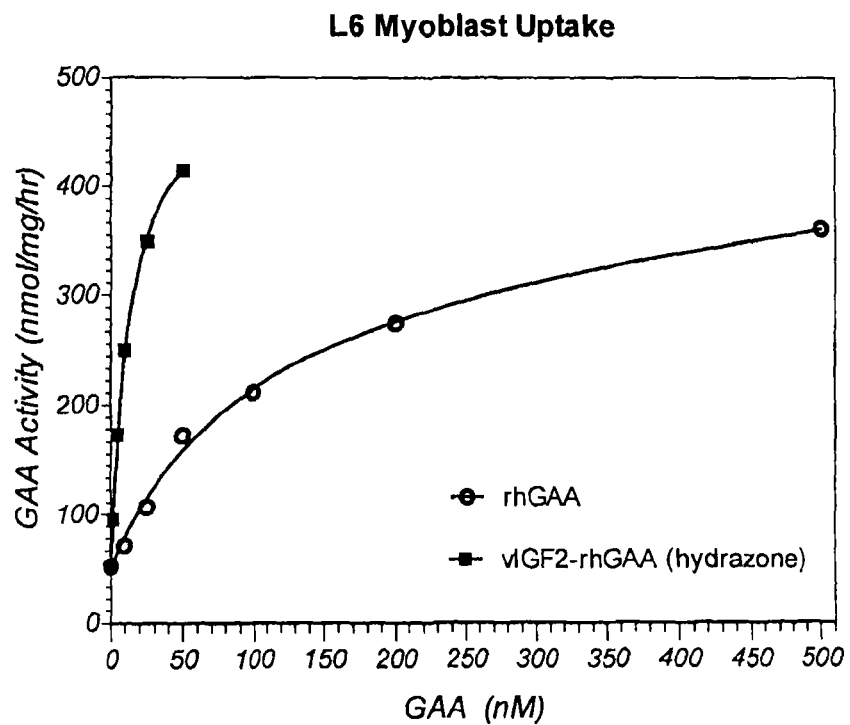
Figure 5B:
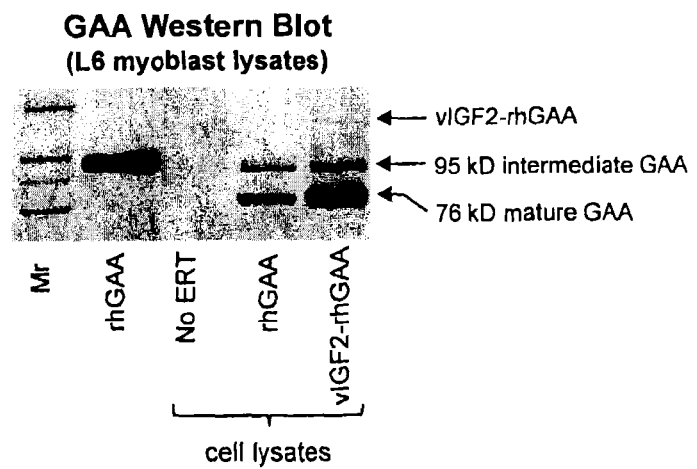

Benzaldehyde-modified rhGAA can be utilized for chemical conjugation to vIGF2 peptide via specific chemical groups such as hydrazide to form a hydrazone linkage as follows. Lyophilized, purified vIGF2 peptide was reconstituted at 0.6 mg/ml in 50 mM sodium phosphate (pH 7.5)/50 mM NaCl/0.05% polysorbate-80 and incubated with a 20-fold molar excess of the bifunctional crosslinker N-tert-butoxycarbonyl (tBoc)-protected hydrazide crosslinker (NHS-PEG4-tBoc-hydrazide; Quanta Biodesign) at ambient temperature to introduce a novel tBoc-protected hydrazide group at the N-terminus. The reaction was monitored by C4 reverse phase high performance liquid chromatography (C4 RP-HPLC) to assess the progression and extent of modification of vIGF2. C4 RP-HPLC method utilized a 4.6×250 mm 5 μm, 300 Å C4 Jupiter column (Phenomenex, Torrence, Calif.) on an Agilent Technologies (Palo Alto, Calif.) HPLC system consisting of a 1100 series quaternary pump, automated sampler, thermo stated column compartment and diode-array detector (DAD) with Agilent ChemStation Software (Rev. B.04.03). Mobile phases consisted of Buffer A: 0.1% trifluoroacetic acid (TFA) in water and Buffer B: 0.1% TFA in acetonitrile (MeCN). Peptide samples were loaded onto C4 column pre-equilibrated with 26% acetonitrile (MeCN/0.1% TFA). After 2 minutes, the column was developed using a 26-33% linear gradient of MeCN/0.1% TFA over 13 minutes. As shown in FIG. 4A, a significant shift (increase) in the retention time is observed upon chemical modification of vIGF2 peptide to attach PEG4-tBoc-hydrazide (middle panel). After completion of chemical modification of vIGF2 peptide (typically by 2 hrs), tBoc-hydrazide-modified vIGF2 peptide was purified by preparative C4 RP-HPLC to remove excess crosslinker and reaction byproducts and lyophilized to remove volatile solvents. The dried peptide was then reconstituted in 2% TFA (in dH$_2$O) and incubated at ambient temperature for up to 72 hrs to remove the tBoc protection group and expose hydrazide group for subsequent conjugation to lysosomal enzymes. The progression of tBoc de-protection was also monitored by C4 RP-HPLC and typically shown to decrease the retention time of peptide upon removal of tBoc to near that of the starting, unmodified vIGF2 peptide (FIG. 4A, bottom panel). Complete de-protection of tBoc group typically required approximately 60 hrs under these experimental conditions. tBoc de-protected hydrazide-modified vIGF2 was then purified by preparative C4 RP-HPLC, lyophilized and stored dry until chemical conjugation to benzaldehyde-modified rhGAA. Removal of the tBoc protecting group has also been tested using higher TFA concentrations (e.g., 4% TFA) and other acids and organic solvents but those conditions led to much lower recovery of hydrazide-modified vIGF2 peptide. De-protected hydrazide vIGF2 peptide was chemically conjugated to benzaldehyde-modified rhGAA (using 4-fold molar excess vIGF2 peptide to rhGAA) via a resultant hydrazone linkage as follows. The protein concentration of benzaldehyde-modified rhGAA was typically adjusted to 4-5 mg/ml with 50 mM sodium phosphate (pH 6.0)/100 mM NaCl/0.05% polysorbate-80 buffer and the enzyme was added directly to lyophilized de-protected hydrazide-modified vIGF2 peptide (at a molar ratio of 1 mole rhGAA:4 moles vIGF2 peptide) and incubated at about 20° C. for approximately 16 hours. Aniline (5-10 mM) can also be added to increase the rate of coupling but we have found that it was not absolutely required for coupling under these experimental conditions. vIGF2 peptide-conjugated rhGAA was then purified by size exclusion chromatography in 50 mM sodium phosphate (pH 6.0)/100 mM NaCl/2% mannitol/0.05% polysorbate-80 buffer to remove excess vIGF2 peptide. Peak fractions of vIGF2-rhGAA were pooled and concentrated using Amicon Ultra with a 30 kDa nominal molecular weight cut-off cellulose acetate membrane. vIGF2-rhGAA was characterized by receptor plate binding assays to determine whether the hydrazone-linked vIGF2 peptide would increase rhGAA binding to the intended IGF2/CI-MPR receptor. As shown in FIG. 4B, vIGF2-rhGAA bound the IGF2/CI-MPR receptor significantly better than unconjugated rhGAA and correlated with substantially better cellular uptake of the exogenous lysosomal enzyme in a skeletal muscle cell model (FIG. 5A). These results show the functional importance of improved receptor binding for enhanced cellular uptake of the exogenous therapeutic drug in target muscle cells. Western blot analysis of muscle cell lysates show that internalized vIGF2-rhGAA was delivered to lysosomes where vIGF2 peptide was removed and rhGAA was processed normally as observed for the unconjugated rhGAA enzyme (FIG. 5B). These results were expected since IGF2 peptide was previously reported to be naturally degraded by resident lysosomal proteases. Importantly, the western blot data indicate that chemically coupled vIGF2 peptide was removed and did not impede GAA processing in lysosomes. (GAA processing is required for high affinity binding and optimal GAA enzyme kinetics for hydrolyzing the natural glycogen substrate).

These collective data therefore confirm that this alternative chemical conjugation can be utilized for generating vIGF2-rhGAA enzyme conjugates which have substantially better binding to the intended IGF2/CI-MPR receptor for improved cellular uptake and delivery of therapeutic drug to lysosomes of target cells. This alternative chemical modification/conjugation procedure generates stable intermediate components that can be stored indefinitely prior to final chemical conjugation and purification. Different batches of stable intermediates can also be pooled to form larger batches for the final conjugation reaction. The methods described herein therefore represent important advancements to enable scale up chemical conjugation process for generating improved ERTs.

Example 5

Figure 6:
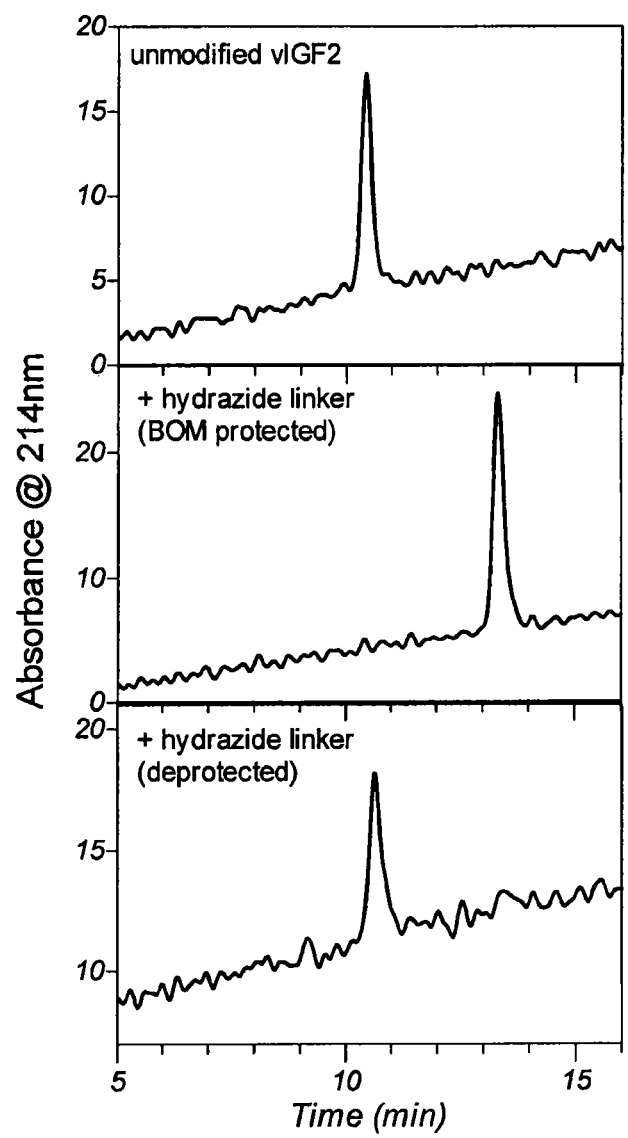

In addition to utilizing tBoc-protected hydrazide crosslinkers for modification of vIGF2 peptide, other crosslinkers with different protection groups can also be utilized. We have chemically synthesized a bifunctional crosslinker containing a methylbenzyloxy carbonyl (BOM)-protected hydrazide (NHS-PEG4-BOM-hydrazide) for introducing a novel hydrazide group to the N-terminus of vIGF2 peptide. After removal of the BOM protection group, the chemically reactive hydrazide group is exposed for subsequent conjugation to benzaldehyde-modified lysosomal enzymes via a resultant hydrazone linkage as follows. Lyophilized, purified vIGF2 peptide was reconstituted at 0.6 mg/ml in 50 mM sodium phosphate (pH 7.5)/50 mM NaCl/0.05% polysorbate-80 and incubated with a 20-fold molar excess of NHS-PEG4-BOM-hydrazide at ambient temperature to introduce a novel BOM-protected hydrazide group at the N-terminus. The reaction was monitored by C4 RP-HPLC to assess the progression and extent of modification of vIGF2. A significant shift (increase) in the retention time is observed upon chemical modification of vIGF2 peptide to attach PEG4-BOM-hydrazide (FIG. 6, middle panel). After completion of chemical modification of vIGF2 peptide (typically by 2 hrs), BOM-hydrazide-modified vIGF2 peptide was purified by preparative C4 RP-HPLC to remove excess crosslinker and reaction byproducts and lyophilized to remove volatile solvents. The dried peptide was then reconstituted in 2% TFA (in dH$_2$O) and incubated at ambient temperature for up to 72 hrs to remove the BOM protection group and expose hydrazide group for subsequent conjugation to lysosomal enzymes. The progression of BOM de-protection was also monitored by C4 RP-HPLC and typically shown to decrease the retention time of peptide upon removal of BOM to near that of the starting, unmodified vIGF2 peptide (FIG. 6, bottom panel). Complete de-protection of BOM group typically required approximately 60 hrs under these experimental conditions. BOM de-protected hydrazide-modified vIGF2 was then purified by preparative C4 RP-HPLC, lyophilized and stored dry until chemical conjugation to benzaldehyde-modified rhGAA.

De-protected hydrazide-modified vIGF2 peptide can then be chemically conjugated to benzaldehyde-modified rhGAA as described above in Example 2 for tBoc-deprotected hydrazide-vIGF2 peptide. These data show that vIGF2 peptide can be chemically modified with bifunctional crosslinkers containing various protected hydrazide groups and after removal of protecting group, the same chemically reactive hydrazide was generated for conjugating vIGF2 peptide to benzaldehyde-modified lysosomal enzymes.

Example 6

Figure 7A:
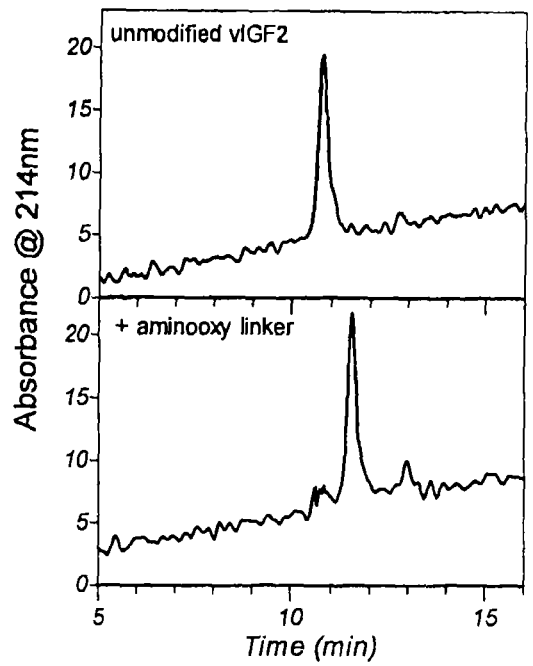
Figure 7B:
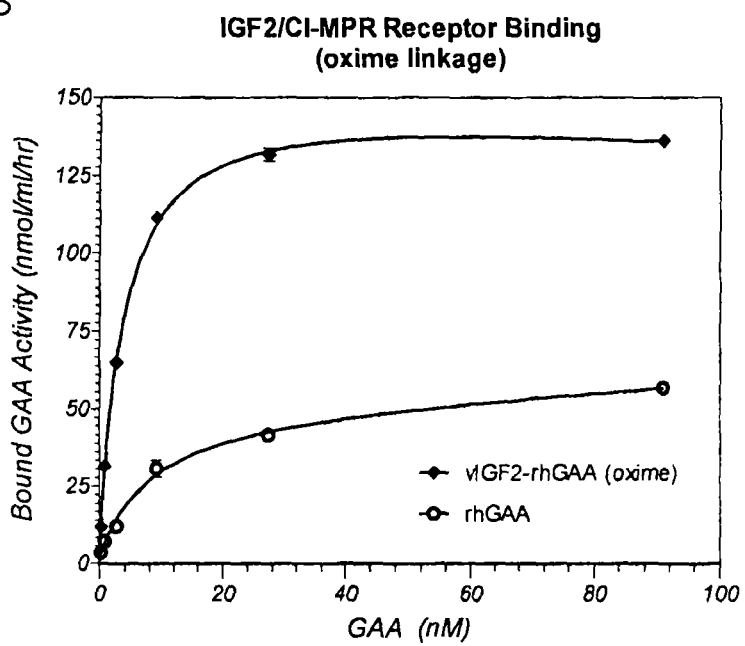

Benzaldehyde-modified rhGAA can also be utilized for chemical conjugation to aminooxy-modified vIGF2 peptide via a very stable oxime linkage as follows. Lyophilized, purified vIGF2 peptide was reconstituted at 0.6 mg/ml in 50 mM sodium phosphate (pH 7.5)/50 mM NaCl/0.05% polysorbate-80 and incubated with a 20-fold molar excess of Phthalimidooxy-PEG12-NHS ester (Quanta Biodesign) at ambient temperature to introduce a novel phthalimidooxy group at the N-terminus. After completion of chemical modification of vIGF2 peptide (typically by 2 hrs), phthalimidooxy-modified vIGF2 peptide was then incubated with 0.5M hydrazine at ambient temperature for 30-60 min to convert the intermediate phthalimidooxy group to the desired aminooxy group. C4 RP-HPLC was utilized for monitoring the chemical modification reaction and the conversion of the phthalimidooxy group to aminooxy group. As shown in FIG. 7A, aminooxy-modified vIGF2 peptide had a slightly longer retention time on C4 RP-HPLC as compared to unmodified vIGF2 peptide. Aminooxy-modified vIGF2 peptide is acidified with TFA and then purified by preparative C4 RP-HPLC to remove excess crosslinker and reaction byproducts and lyophilized to remove volatile solvents. The dried aminooxy-modified hydrazide vIGF2 peptide was used directly for chemically conjugation to benzaldehyde-modified rhGAA via a resultant oxime linkage. Briefly, the protein concentration of benzaldehyde-modified rhGAA was typically adjusted to 4-5 mg/ml with 50 mM sodium phosphate (pH 6.0)/100 mM NaCl/0.05% polysorbate-80 buffer and the enzyme was added directly to the dry aminooxy-modified vIGF2 peptide (at a molar ratio of 1 mole rhGAA:4 moles vIGF2 peptide) and incubated at about 20° C. for approximately 16 hours. vIGF2 peptide-conjugated rhGAA was then purified by size exclusion chromatography in 50 mM sodium phosphate (pH 6.0)/100 mM NaCl/2% mannitol/0.05% polysorbate-80 buffer to remove excess vIGF2 peptide as described before.

vIGF2-rhGAA was characterized by receptor plate binding assays to determine whether the oxime-linked vIGF2 peptide would increase rhGAA binding to the intended IGF2/CI-MPR receptor. As shown in FIG. 7B, vIGF2-rhGAA bound the IGF2/CI-MPR receptor substantially better than unconjugated rhGAA. In addition, the oxime linkage is very stable and ensures that vIGF2 peptide remains conjugated to rhGAA and is only removed upon its degradation in lysosomes after delivery of therapeutic drug.

Figure 8:
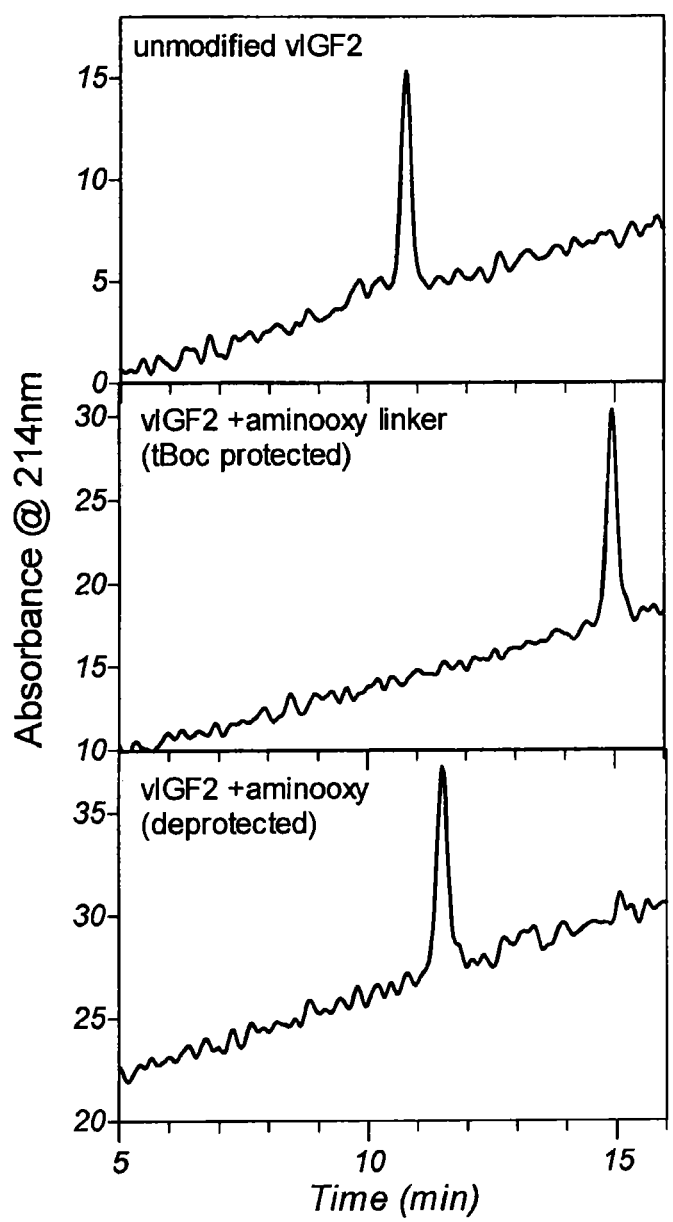
Figure 9:
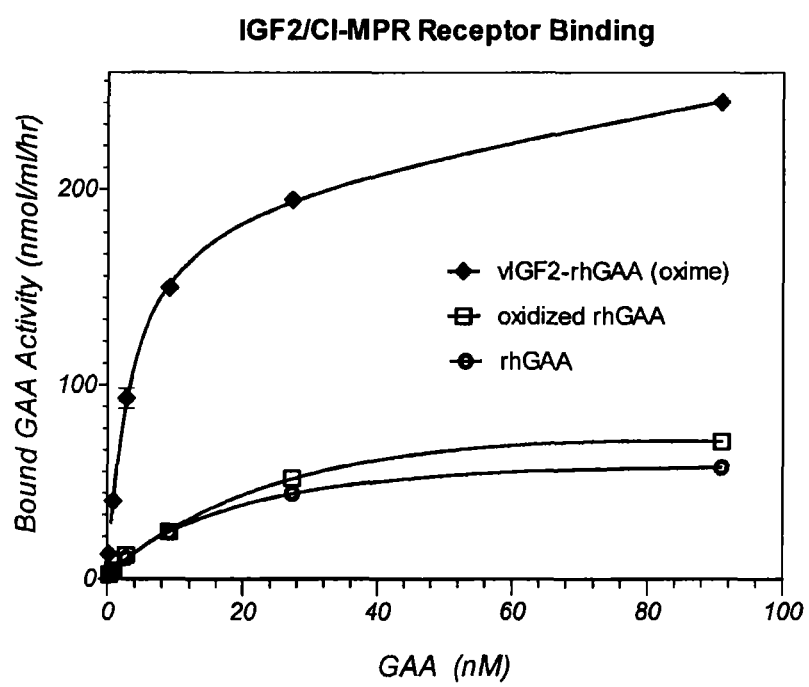

Example 7 vIGF2 peptide can also be chemically conjugated to lysosomal enzymes via an oxime linkage using tBoc-protected aminooxy bifunctional crosslinker. This approach yields aminooxy-modified vIGF2 peptide for chemical conjugation to benzaldehyde-modified lysosomal enzymes without requiring chemical conversion using potentially dangerous hydrazine. Briefly, lyophilized, purified vIGF2 peptide was reconstituted at 0.6 mg/ml in 50 mM sodium phosphate (pH 7.5)/50 mM NaCl/0.05% polysorbate-80 and incubated with a 20-fold molar excess of the bifunctional crosslinker tBoc-protected aminooxy crosslinker (with either NHS— or pentafluorobenzene group) at ambient temperature to introduce a novel tBoc-protected aminooxy group at the N-terminus and monitored by C4 RP-HPLC. As shown in FIG. 8 (middle panel), a significant shift (increase) in the retention time is observed upon chemical modification of vIGF2 peptide to attach PEGylated tBoc-aminooxy crosslinker (middle panel). After completion of chemical modification of vIGF2 peptide (typically by 2 hrs), tBoc-aminooxy-modified vIGF2 peptide was purified by preparative C4 RP-HPLC to remove excess crosslinker and reaction byproducts and lyophilized to remove volatile solvents. The dried peptide was then reconstituted in 2% TFA (in dH$_2$O) and incubated at ambient temperature for up to 72 hrs to remove the tBoc protection group and expose aminooxy group for subsequent conjugation to lysosomal enzymes. The progression of tBoc de-protection was also monitored by C4 RP-HPLC and typically shown to decrease the retention time of peptide upon removal of tBoc to near that of the starting, unmodified vIGF2 peptide (FIG. 8, bottom panel). Complete de-protection of tBoc group typically required approximately 50 hrs under these experimental conditions. tBoc de-protected aminooxy-modified vIGF2 was then purified by preparative C4 RP-HPLC, lyophilized and stored dry until chemical conjugation to benzaldehyde-modified lysosomal enzymes.

Example 8

An alternative method to generate oxime linked vIGF2-rhGAA using a single crosslinker can be achieved by coupling aminooxy-modified vIGF2 peptide to chemically oxidized rhGAA as follows. rhGAA was buffer exchanged into 0.1M NaOAc (pH 5.2) via dialysis or size exclusion chromatography (SEC) and the protein concentration was adjusted to 5 mg/ml with same buffer. rhGAA was then incubated with 2 mM sodium meta-periodate at 4° C. for 30 min to oxidize carbohydrates (mostly terminal sialic acids and galactose) on N-glycans of rhGAA to generate chemically reactive aldehyde groups for chemical conjugation to aminooxy-modified vIGF2 peptide. Chemically oxidized rhGAA was then dialyzed against 0.1M NaOAc (pH 5.2) or subjected to SEC to remove excess sodium meta-periodate. Oxidized rhGAA (stored at approximately 4 mg/ml) was added directly to the dry aminooxy-modified vIGF2 peptide at a molar ratio of 1 mole rhGAA:4 moles vIGF2 peptide and incubated at about 20° C. for approximately 16 hours to form the resultant oxime linkage. vIGF2 peptide-conjugated rhGAA was then purified by SEC in 50 mM sodium phosphate (pH 6.0)/100 mM NaCl/2% mannitol/0.05% polysorbate-80 buffer to remove excess vIGF2 peptide as described before.

vIGF2-rhGAA was characterized by receptor plate binding assays to determine whether the oxime-linked vIGF2 peptide would increase rhGAA binding to the intended IGF2/CI-MPR receptor. As shown in FIG. 9, vIGF2-rhGAA bound the IGF2/CI-MPR receptor substantially better than unconjugated rhGAA. The improved receptor binding was dependent on the presence of vIGF2 since oxidized rhGAA (lacking vIGF2 peptide) was shown to have similar binding as the starting unconjugated rhGAA enzyme. The receptor binding data also suggest that more vIGF2 peptides were conjugated to chemically oxidized rhGAA than SFB (benzaldehyde)-modified rhGAA. Since there are more terminal carbohydrates on N-glycans which are fully accessible and can be chemically oxidized to form aldehydes, there is high potential for conjugation to more vIGF2 peptides as compared to SFB-modified rhGAA (which introduces an average of 2 benzaldehyde groups for coupling to vIGF2 peptide using the described procedure herein). These results therefore confirm that aminooxy-modified vIGF2 peptide can be utilized for coupling to aldehyde-containing lysosomal enzymes for improved binding to the intended IGF2/CI-MPR receptor for better delivery of therapeutic drug.

What is claimed:

1. A method of chemical conjugation comprising:
   a. contacting a lysosomal enzyme with a first crosslinking agent to introduce aldehyde groups;
   b. contacting a lysosomal targeting peptide with a second crosslinking agent to introduce a hydrazide group at the N-terminal residue;
   c. contacting the lysosomal enzyme with aldehyde groups of a with the lysosomal targeting peptide with a hydrazide group at the N-terminal residue of b; and
   d. forming a lysosomal enzyme-lysosomal targeting peptide conjugate.

2. The method of claim 1 wherein the lysosomal targeting peptide comprises variant insulin-like growth factor 2 (vIGF2) having the sequence of SEQ ID NO:1, SEQ ID NO:2, SEQ ID NO:3, or SEQ ID NO:4.

3. The method of claim 1, wherein the first crosslinking agent comprises N-succinimidyl-4-formylbenzamide (S-4FB).

4. The method of claim 1, wherein the second crosslinking agent comprises N-tert-butoxycarbonyl (tBoc)-protected hydrazide crosslinker (NHS-PEG4-tBoc-hydrazide).

5. The method of claim 1, wherein the lysosomal enzyme comprises acid α-glucosidase (rhGAA), acid α-galactosidase A (GLA), acid β-glucuronidase (GUS), acid α-iduronidase A (IduA), acid iduronidate 2-sulfatase (I2S), β-hexosaminidase A (HexA), β-hexosaminidase B (HexB), acid α-mannosidase A, β-glucocerebrosidase (GlcCerase), acid lipase (LPA), or any combination thereof.

6. The method of claim 1, wherein the lysosomal enzyme is human.

7. The method of claim 1, wherein the lysosomal targeting peptide with a hydrazide group at the N-terminal residue is added in c at about four-fold molar excess.

8. The method of claim 1, wherein aniline is added in c.

* * * * *

SEQUENCE LISTING

```
<160> NUMBER OF SEQ ID NOS: 4

<210> SEQ ID NO 1
<211> LENGTH: 67
<212> TYPE: PRT
<213> ORGANISM: Artificial Sequence
<220> FEATURE:
<223> OTHER INFORMATION: Synthetic peptide

<400> SEQUENCE: 1

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65

<210> SEQ ID NO 2
<211> LENGTH: 63
<212> TYPE: PRT
<213> ORGANISM: Artificial Sequence
<220> FEATURE:
<223> OTHER INFORMATION: Synthetic peptide

<400> SEQUENCE: 2

Ser Arg Thr Leu Cys Gly Gly Glu Leu Val Asp Thr Leu Gln Phe Val
1               5                   10                  15

Cys Gly Asp Arg Gly Phe Leu Phe Ser Arg Pro Ala Ser Arg Val Ser
            20                  25                  30

Arg Arg Ser Arg Gly Ile Val Glu Glu Cys Cys Phe Arg Ser Cys Asp
        35                  40                  45

Leu Ala Leu Leu Glu Thr Tyr Cys Ala Thr Pro Ala Arg Ser Glu
```

```
                50                  55                  60

<210> SEQ ID NO 3
<211> LENGTH: 67
<212> TYPE: PRT
<213> ORGANISM: Artificial Sequence
<220> FEATURE:
<223> OTHER INFORMATION: Synthetic peptide

<400> SEQUENCE: 3

Gly Gly Gly Gly Ser Arg Thr Leu Cys Gly Gly Glu Leu Val Asp Thr
1               5                   10                  15

Leu Gln Phe Val Cys Gly Asp Arg Gly Phe Leu Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Arg Ser Glu
65

<210> SEQ ID NO 4
<211> LENGTH: 72
<212> TYPE: PRT
<213> ORGANISM: Artificial Sequence
<220> FEATURE:
<223> OTHER INFORMATION: Synthetic peptide

<400> SEQUENCE: 4

Gly Gly Gly Gly Ser Gly Gly Gly Gly Ser Arg Thr Leu Cys Gly Gly
1               5                   10                  15

Glu Leu Val Asp Thr Leu Gln Phe Val Cys Gly Asp Arg Gly Phe Leu
            20                  25                  30

Phe Ser Arg Pro Ala Ser Arg Val Ser Arg Arg Ser Arg Gly Ile Val
        35                  40                  45

Glu Glu Cys Cys Phe Arg Ser Cys Asp Leu Ala Leu Leu Glu Thr Tyr
    50                  55                  60

Cys Ala Thr Pro Ala Arg Ser Glu
65                  70
```